US00PP28788P2

(12) United States Plant Patent
Korlipara

(10) Patent No.: US PP28,788 P2
(45) Date of Patent: Dec. 19, 2017

(54) ***ECHINACEA* PLANT NAMED 'TNECHPV'**

(50) Latin Name: ***Echinacea* hybrid**
Varietal Denomination: TNECHPV

(71) Applicant: Terra Nova Nurseries, Inc., Canby, OR (US)

(72) Inventor: Harini Korlipara, Canby, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 18 days.

(21) Appl. No.: 14/999,900

(22) Filed: Jul. 14, 2016

(51) Int. Cl.
*A01H 5/02* (2006.01)

(52) U.S. Cl.
USPC ..... Plt./428

(58) Field of Classification Search
USPC ..... Plt./263.1, 428
See application file for complete search history.

*Primary Examiner* — Susan McCormick Ewoldt
*Assistant Examiner* — Karen Redden
(74) *Attorney, Agent, or Firm* — Klarquist Sparkman, LLP

(57) ABSTRACT

A new and distinct *Echinacea* plant named 'TNECHPV' characterized by large inflorescences with white ray florets and light yellow disc florets, enlarged disc florets forming an anemone-type double inflorescence, one to five inflorescences per stem, a broad mounding habit with excellent stem number from crown, and excellent vigor.

2 Drawing Sheets

Botanical denomination: *Echinacea* hybrid.
Variety designation: 'TNECHPV'.

BACKGROUND OF THE INVENTION

The present invention relates to a new and distinct cultivar of *Echinacea* and given the cultivar name 'TNECHPV'. *Echinacea* is in the family Asteraceae. The new cultivar is part of a planned breeding program for a series with compact habits and double "anemone"-type inflorescences. The exact parents of this selection are unknown, unnamed, proprietary interspecific hybrids.

Compared to *Echinacea* 'White Double Delight' (U.S. Plant Pat. No. 23,472), the new cultivar has larger inflorescences and habit and orange centers rather than green on young inflorescences.

Compared to *Echinacea* 'Milkshake' (U.S. Plant Pat. No. 20,594), the new cultivar has larger inflorescences, a wider habit, and shorter peduncles.

Compared to *Echinacea* 'Vanilla Cupcake' (U.S. Plant Pat. No. 24,506), the new cultivar has a larger habit, broader cones, shorter and more uniform ray florets, and orange centers rather than green on young inflorescences.

This new *Echinacea* cultivar is distinguished by:

1. large inflorescences with white ray florets and light yellow disc florets,
2. enlarged disc florets forming an anemone-type double inflorescence,
3. one to five inflorescences per stem,
4. a broad mounding habit with excellent stem number from crown, and
5. excellent vigor.

This new cultivar has been reproduced only by asexual propagation (division and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

FIG. 2 shows the immature inflorescences of *Echinacea* 'TNECHPV'.

FIG. 3 shows a close up of the flowers of *Echinaceae* 'TNECHPV'.

DETAILED PLANT DESCRIPTION

Figure 1:
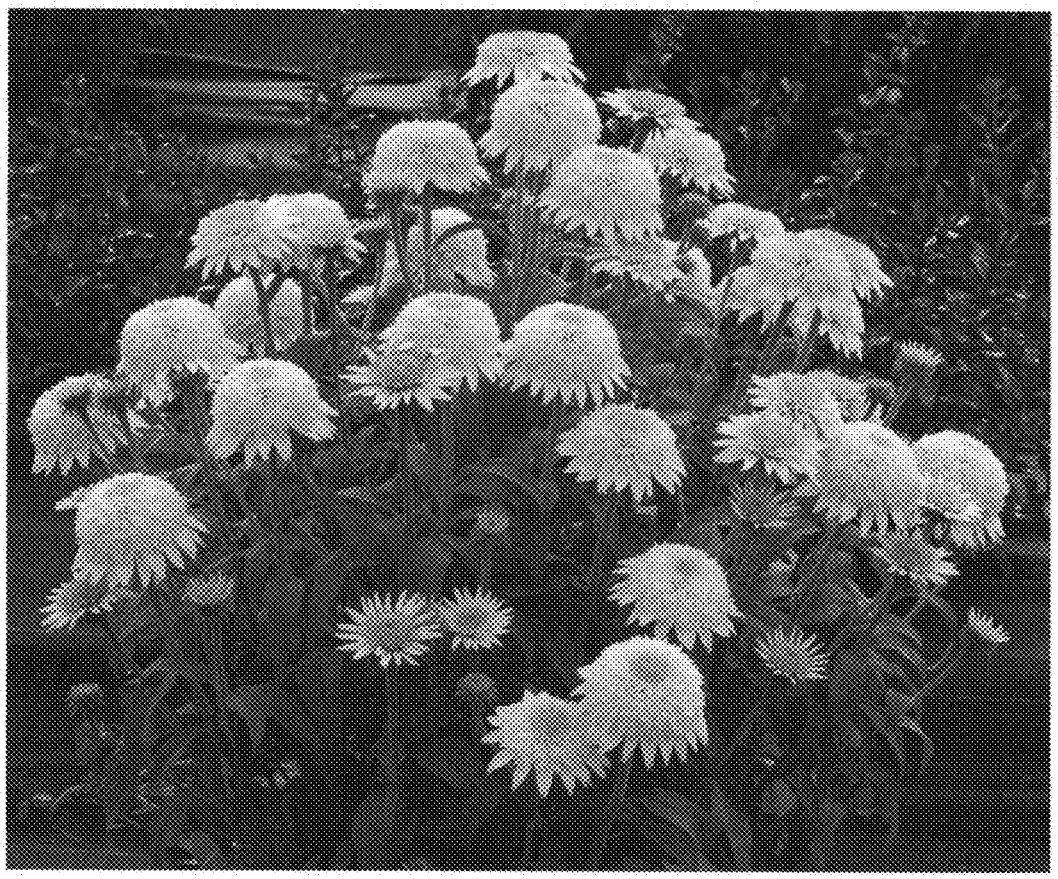
FIG. 1 shows a two-year-old plant of *Echinacea* 'TNECHPV' growing in the trial bed in flower in full sun in early July in Canby, Oreg.

The following is a detailed description of the new *Echinacea* cultivar based on observations of two-year-old specimens growing in the trial beds in full sun in Canby, Oreg. Canby is in Zone 8 on the USDA Hardiness map. Temperatures range from a high of 95 degrees F. in August to an average of 32 degrees F. in January. Normal rainfall in Canby is 42.8 inches per year in the trial fields in Canby, Oreg. The color descriptions are all based on *The Royal Horticultural Society Colour Chart,* $5^{th}$ edition, 2007.

Plant:

*Type*.—Herbaceous perennial.

*Hardiness*.—USDA Zones 4 to 9.

*Size*.—Grows to about 78 cm wide and 67 cm tall to top of inflorescences.

*Form*.—Basal clump, with about 25 stems from the base.

*Vigor*.—Excellent.

*Roots*.—Fibrous, with many downward growing and few laterals, ivory in color, Yellow White 158D, roots develop easily from cuttings from the crown.

Stem (flowering):

*Type*.—Ascending, with 1 to 5 inflorescences per stem.

*Size*.—To 58 cm tall to a terminal inflorescence and 10 mm wide at base.

*Internode length*.—5 cm to 14 cm.

*Surface texture*.—Strigose.

*Color*.—Yellow Green 146B.

Leaf (basal):

*Type*.—Simple.

*Shape*.—Lanceolate.

*Arrangement*.—Basal.

*Blade size*.—Grows to 11 cm long and 5 cm wide.

*Margins*.—Sparsely serrate.

*Apex*.—Acute.

*Base*.—Attenuate.

*Surface texture*.—Strigose on both sides.

*Venation*.—Pinnate, with 3 main veins from the base, Yellow Green 147D on topside where visible and 145C on bottom side.

*Color*.—Topside, Green N137A, bottom side Green N137B.

*Petiole description*.—Grows to 15 cm long and 4 mm wide above the clasp, sparsely strigose, Yellow Green 147C.

Leaf (stem):

*Type*.—Simple.

*Shape*.—Lanceolate.

*Arrangement*.—Alternate.

*Blade size*.—Grows to 11.5 cm long and 5 cm wide.

*Margins*.—Sparsely serrate.

*Apex*.—Acuminate.

*Base*.—Attenuate.

*Surface texture*.—Strigose on both sides.

*Venation*.—Pinnate, with 3 main veins from the base, Yellow Green 147D on topside where visible and 145C on bottom side.

*Color*.—Topside, Green N137A, bottom side Green N137B.

*Petiole description*.—On all but uppermost leaves, clasping, grows to 7 cm long and 3 mm wide above the clasp, strigose, topside, Yellow Green 147C.

Inflorescence:

*Type*.—Composite on terminal stalked heads.

*Number of flowering stems from the ground*.—About 47.

*Flowering stem*.—Grows to 58 cm tall from the base of the plant to the terminal inflorescence and can grow to 10 cm long from the top stem leaf to the base of an inflorescence; branched with 1 to 5 inflorescences per stem; diameter growing to 7 mm wide near the inflorescence; strigose; Yellow Green 146B.

*Size*.—Grows to 8.5 cm wide and 6 cm deep as disc enlarges.

*Form*.—Ray florets held slightly to strongly reflexed, mature disc is conic.

*Immature inflorescence* ("*flower bud*").—Grows to 3.5 cm wide and 1.5 cm deep, ray florets held at a 1 to 20 degree angle from the horizontal and rolled up so only the back color shows, closest to Green Yellow 1C, disc color Yellow Orange 18A over Yellow Green 145B.

*Ray florets*.—Without pistil or stamen, from 22 to 29 in number, grow to 38 mm long and 12 mm wide, elliptic to lanceolate with the tip two to three-toothed, teeth grow 3 to 10 mm long and 1 to 4 mm wide, tips acute; margins entire, base attenuate, glabrous on both sides; top side White NN155A with tip edges and base Yellow Green 145C, bottom side White NN155A tinted Yellow Green 145C.

*Disc*.—Flat becoming conic, growing to 40 mm deep and 65 mm wide with maturity, center Yellow Orange 22B, Yellow 11C when disc florets are open.

*Disc florets*.—To about 450 in number, each with 1 pistil and 4 stamen, grow to 28 mm long and 10 mm wide, each with one persistent, very stiff linear bract (14 mm long with top 4 mm Yellow Orange 17A to 5 mm Yellow Green 145A to White NN155C on bottom); corollas to 24 mm long and 10 mm wide, tubular at base (to 5.5 mm long and 1.5 mm wide, Yellow Green 145A) then opens to a 4-toothed fan or 3-toothed fan and 1 side lobe, fan is oblanceolate to obovate and grows to 18 mm long and 10 mm wide with teeth 2 to 9 mm deep and 1 mm wide, (side lobe lanceolate, cut to the tube, to 17 mm long and 4 mm wide); margins entire, tips acute, bases attenuate, glabrous on both sides, topside young florets White NN155A with tips Yellow Green 1445A, bottom side Yellow Green 145C; pistil 10 mm long, ovary 3 mm long, White NN155A with top Yellow Green 145A, style 7 mm long Yellow Green 145D, 2-branched stigma spreading, Yellow Orange 14C; stamen reduced, 2.5 mm long, filaments 2 mm long, thread-like, White 155A, anthers dry, no pollen, male sterile.

*Phyllaries*.—In 3 leafy series, about 70 in number, area grows to 36 mm wide and 15 mm deep, lobes lanceolate in shape, reflexed, grow to 14 mm long and 34 mm wide, top side Yellow Green 147A, bottom side 147B, margins entire, tip acute, both surfaces strigose.

*Receptacle*.—Grows to 16 mm wide and 17 mm deep, White NN155B.

*Bloom period*.—June through October in Canby, Oreg.

*Fragrance*.—Slight, sweet.

*Lastingness*.—Each inflorescence lasts about three weeks in Canby, Oreg.

*Seeds*.—None seen.

*Fertility*.—Poor.

Disease and pests: No pests or diseases have been observed on plants grown under commercial conditions in Canby, Oreg. No resistances are known.

I claim:

1. A new and distinct *Echinacea* plant as herein illustrated and described.

* * * * *

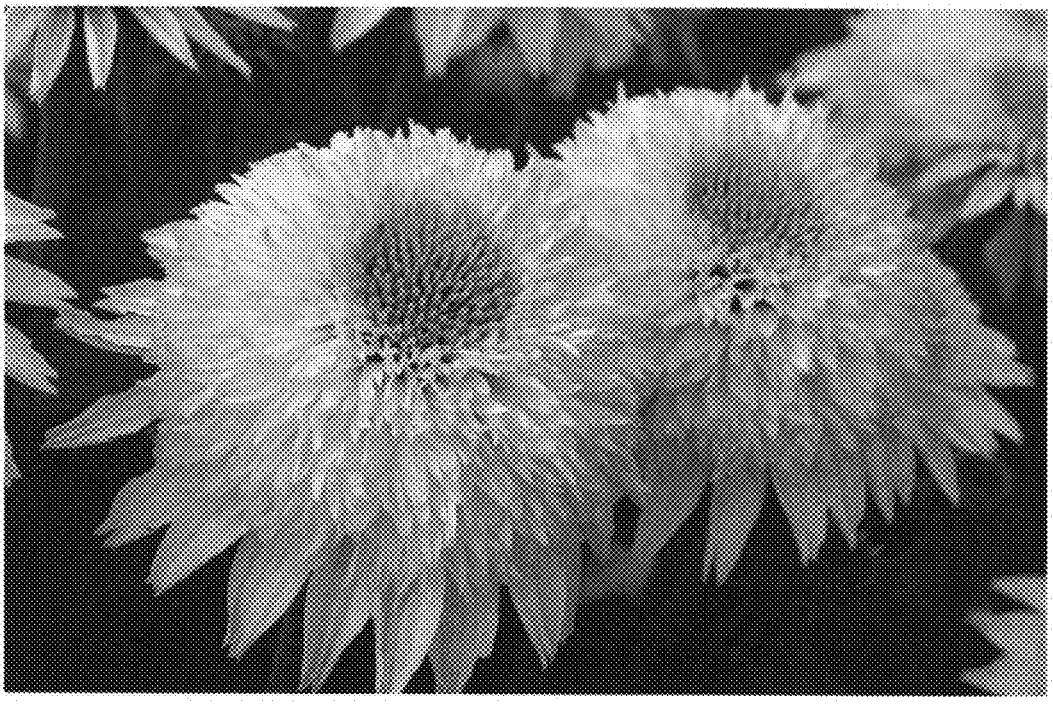

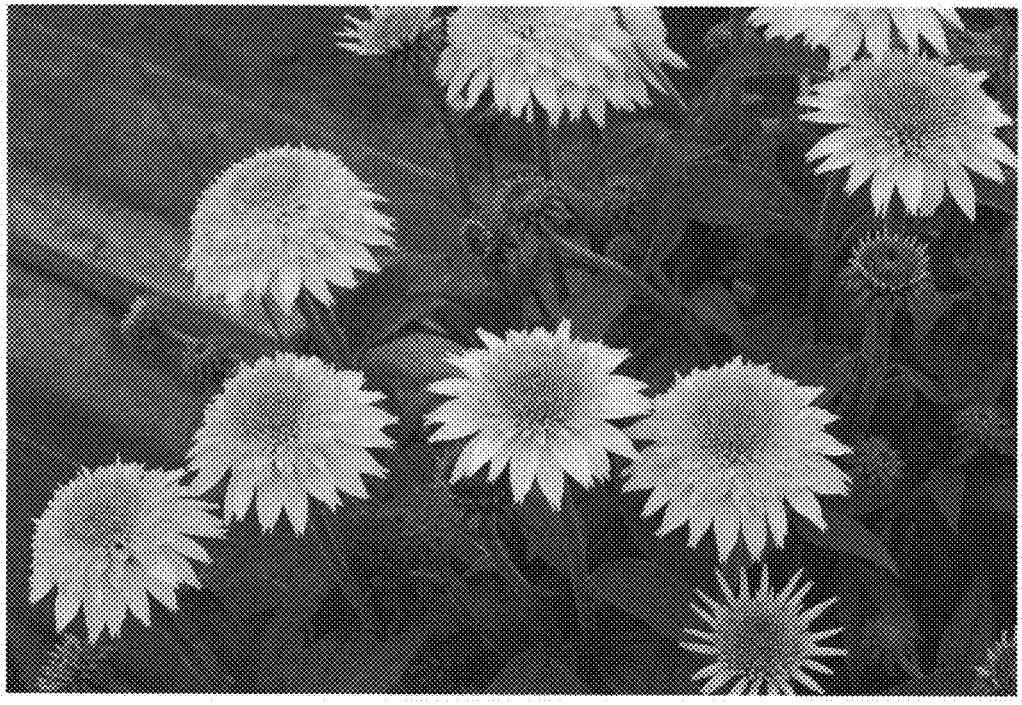
FIG. 2 above, FIG. 3 below